United States Patent
Rubino et al.

(10) Patent No.: US 9,687,451 B2
(45) Date of Patent: Jun. 27, 2017

(54) CONTROLLED RELEASE MATRIX PHARMACEUTICAL DOSAGE FORMULATION

(75) Inventors: Orapin P. Rubino, Towaco, NJ (US); David M. Jones, Ramsey, NJ (US)

(73) Assignee: GLATT AIR TECHNIQUES, INC., Ramsey, NJ (US)

( * ) Notice: Subject to any disclaimer, the term of this patent is extended or adjusted under 35 U.S.C. 154(b) by 387 days.

(21) Appl. No.: 12/661,670

(22) Filed: Mar. 22, 2010

(65) Prior Publication Data

US 2010/0255090 A1  Oct. 7, 2010

Related U.S. Application Data

(63) Continuation of application No. 11/628,890, filed as application No. PCT/US2005/020203 on Jun. 8, 2005, now abandoned.

(60) Provisional application No. 60/578,930, filed on Jun. 10, 2004.

(51) Int. Cl.
*A61K 9/16* (2006.01)
*A61K 9/20* (2006.01)
*A61K 31/138* (2006.01)
*A61K 31/192* (2006.01)

(52) U.S. Cl.
CPC .......... *A61K 9/1676* (2013.01); *A61K 9/1611* (2013.01); *A61K 9/1635* (2013.01); *A61K 9/1652* (2013.01); *A61K 9/2027* (2013.01); *A61K 9/2054* (2013.01); *A61K 9/2077* (2013.01); *A61K 31/138* (2013.01); *A61K 31/192* (2013.01); *A61K 9/2013* (2013.01)

(58) Field of Classification Search
CPC .............. A61K 2300/00; A61K 9/2077; A61K 9/1676; A61K 31/00; A61K 45/06; A61K 31/13; A61K 31/131; A61K 31/221; A61K 31/225; A61K 31/351; A61K 31/366; A61K 31/40; A61K 31/403; A61K 31/445; A61K 31/485; A61K 31/505; A61K 31/57

See application file for complete search history.

(56) References Cited

U.S. PATENT DOCUMENTS

| | | | | |
|---|---|---|---|---|
| 5,260,073 | A * | 11/1993 | Phipps | 424/465 |
| 6,110,500 | A * | 8/2000 | Kim | 424/475 |
| 6,132,769 | A * | 10/2000 | Remon et al. | 424/464 |
| 6,449,869 | B1 * | 9/2002 | Bretschneider et al. | 34/59 |
| 6,517,868 | B2 * | 2/2003 | Fassihi et al. | 424/470 |
| 6,569,463 | B2 * | 5/2003 | Patel et al. | 424/497 |
| 6,596,311 | B1 * | 7/2003 | Dobetti | 424/464 |
| 6,607,751 | B1 * | 8/2003 | Odidi et al. | 424/488 |
| 2002/0155067 | A1 * | 10/2002 | MacGregor | 424/44 |
| 2003/0059471 | A1 * | 3/2003 | Compton et al. | 424/489 |
| 2003/0143257 | A1 * | 7/2003 | Fleshner-Barak et al. | 424/426 |
| 2003/0219482 | A1 * | 11/2003 | Chaudhari et al. | 424/469 |
| 2004/0185111 | A1 * | 9/2004 | Rubino et al. | 424/489 |
| 2008/0254115 | A1 * | 10/2008 | Rubino | 424/456 |

OTHER PUBLICATIONS

Khan et al (Journal of Controlled Release, 1999, vol. 57, pp. 197-203).*
Russo et al (PR Health Sciences Journal, 2000, vol. 19, pp. 131-137).*

* cited by examiner

*Primary Examiner* — Mark V Stevens
(74) *Attorney, Agent, or Firm* — Haug Partners LLP

(57) ABSTRACT

A compressed tablet of a pharmaceutical compound which contains uncoated pellets containing a pharmaceutical compound, where the uncoated pellets are dispersed in a matrix containing the pellets and a swellable polymer.

24 Claims, 4 Drawing Sheets

CONTROLLED RELEASE MATRIX PHARMACEUTICAL DOSAGE FORMULATION

This application is a continuation of Ser. No. 11/628,890, filed Dec. 6, 2006 now abandoned which is a national stage application of PCT/US2005/020203, filed Jun. 8, 2005 which claims priority from Application Ser. 60/578,930, filed Jun. 10, 2004.

BACKGROUND OF THE INVENTION

Oral solid dosage forms have been described in the prior art which are based on pellets which are dispersed in a matrix which is compressed into a tablet. U.S. Pat. No. 5,637,320 describes a formulation where pellets of naproxen are coated with a multilayer membrane which controls the release of the naproxen. The present applicant has discovered that it is not necessary to provide coated pellets in a compressed tablet matrix to obtain controlled release properties of a drug contained in the pellets if the matrix is formulated to contain a swellable pharmaceutical polymer.

Typically, in the prior art, pellets have been used in formulations for sustained or controlled release where the pellets are coated with controlled or modified release polymers to obtain a sustained or controlled release dosage form. It has been discovered that uncoated drug pellets, when combined with a matrix comprising a swellable or controlled release polymer will provide extended release of the pharmaceutical compound.

A compressed tablet, made with a controlled release polymer in the matrix, which is preferably a carbomer, in combination with uncoated drug containing pellets can provide a controlled release including zero-order release formulations suitable for 8-24 hour dosing, depending on the drug and the desired frequency of dosing.

SUMMARY OF THE INVENTION

The invention provides a novel compressed tablet formulation of a pharmaceutically active compound which comprises uncoated pellets containing a pharmaceutical compound which are dispersed in a matrix which comprises said pellets and a swellable polymer which is compressed into a tablet.

Accordingly it is an object of the invention to provide a controlled release formulation of a pharmaceutically active compound.

It is also an object of the invention to provide a zero order controlled release formulation of a pharmaceutically active compound which will permit 8-24 hour dosing.

These and other objects of the invention will be apparent from the specification.

As used herein the term "pellet" means a substantially spherically shaped particle having a aspect ratio (a ratio of the length of the pellet divided by the width found at an angle of 90° in respect to the length) which is less than about 1.4, more preferably less than about 1.3, even more preferably less than about 1.2, especially preferably less than about 1.1, and most preferably less than about 1.05.

DETAILED DESCRIPTION OF THE INVENTION

Figure 1:
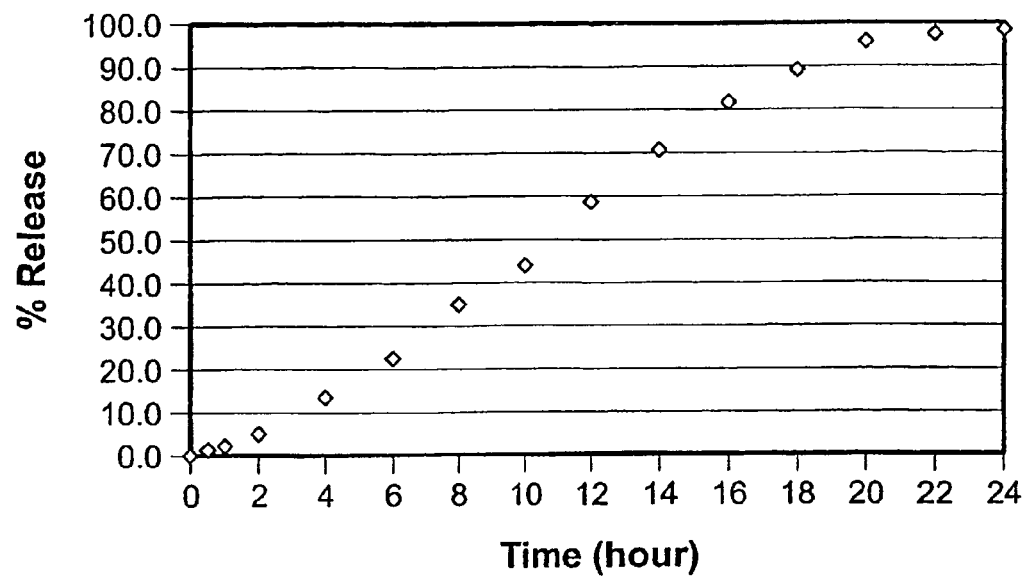
FIG. 1 is a dissolution profile of the oxybuytynin chloride tablets of Example 1.
Figure 2:
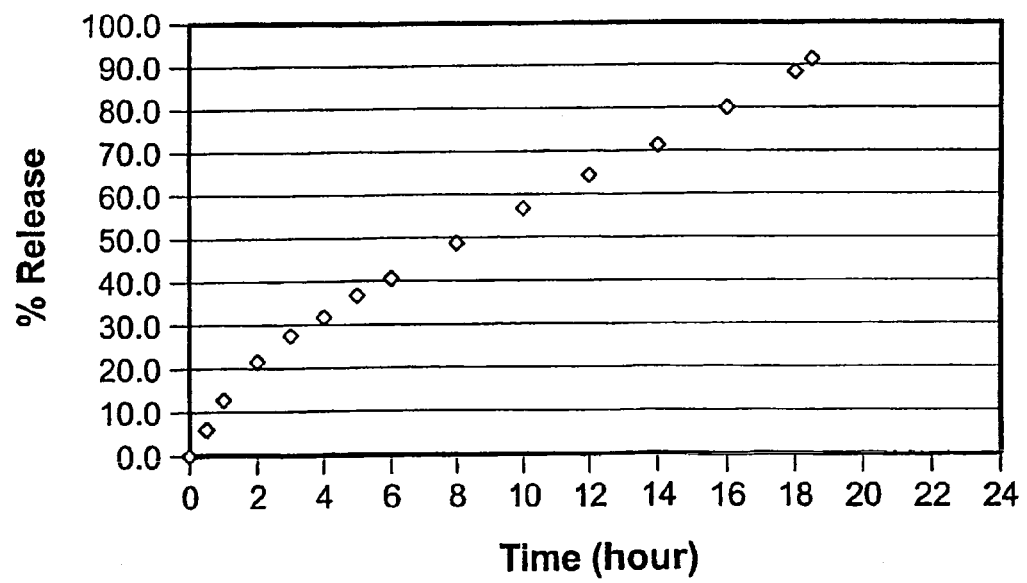
FIG. 2 is a dissolution profile of propranolol hydrochloride tablets made with pellets made according to the procedure of Example 1.
Figure 3:
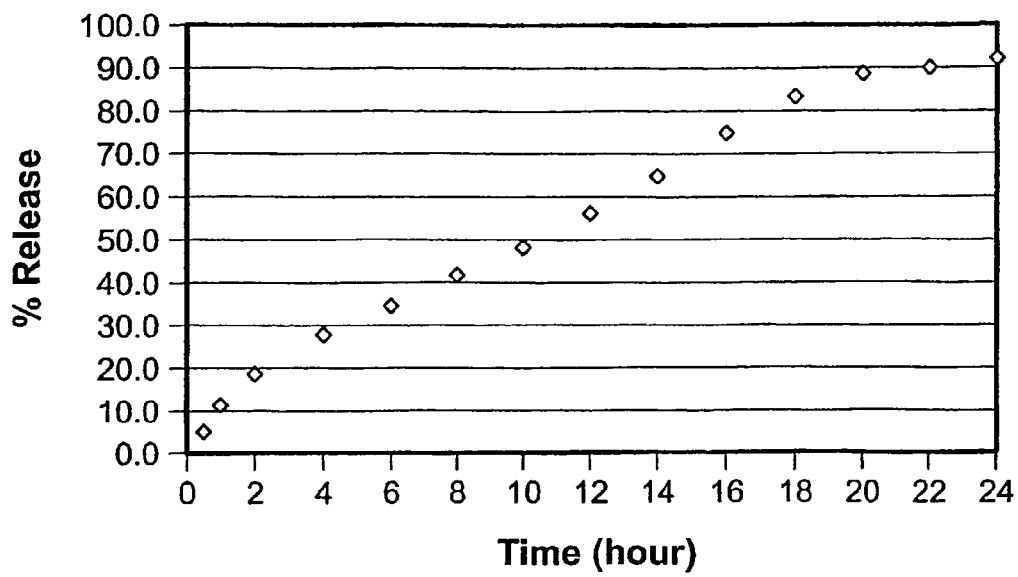
FIG. 3 is a dissolution profile of the propranolol hydrochloride tablets of Example 3 where the pellets were made by extrusion spheronization.
Figure 4:
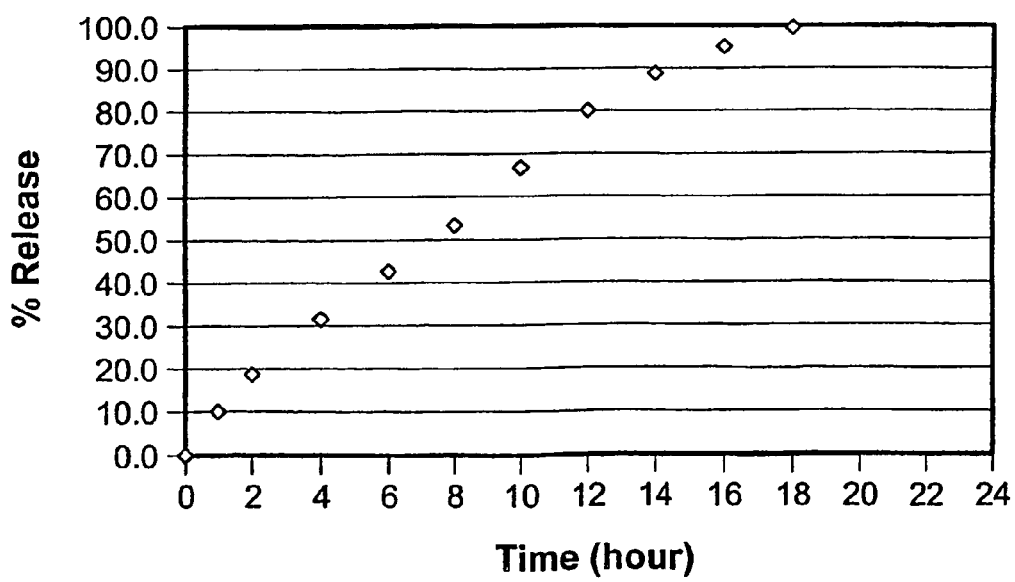
FIG. 4 is a dissolution profile of the metoprolol succinate extended release tablets of Example 4 where the pellets were made by suspension layering.
Figure 5:
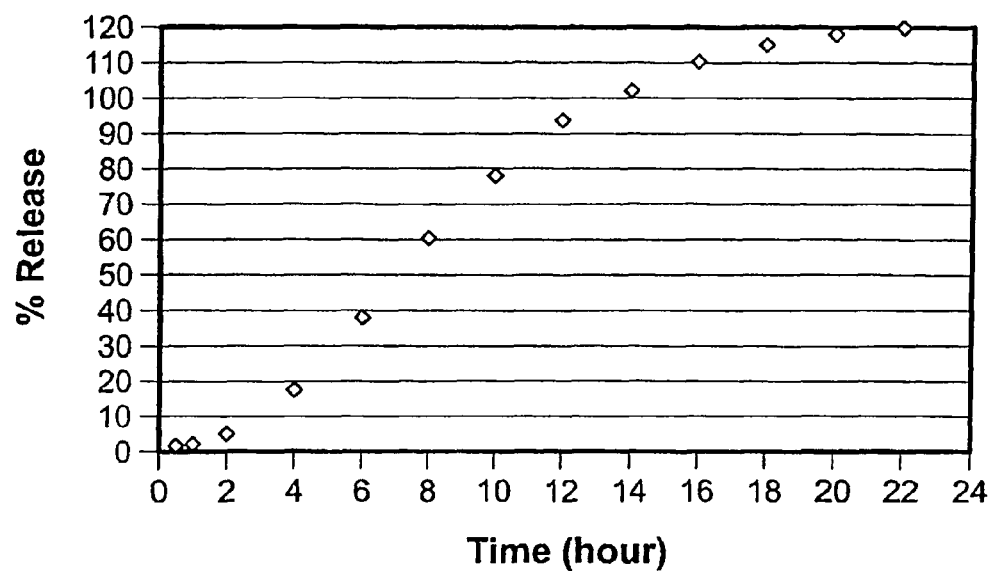
FIG. 5 is a dissolution profile of the ibuprofen tablets of Example 5 where the pellets were made by the procedure of Example 1.
Figure 6:
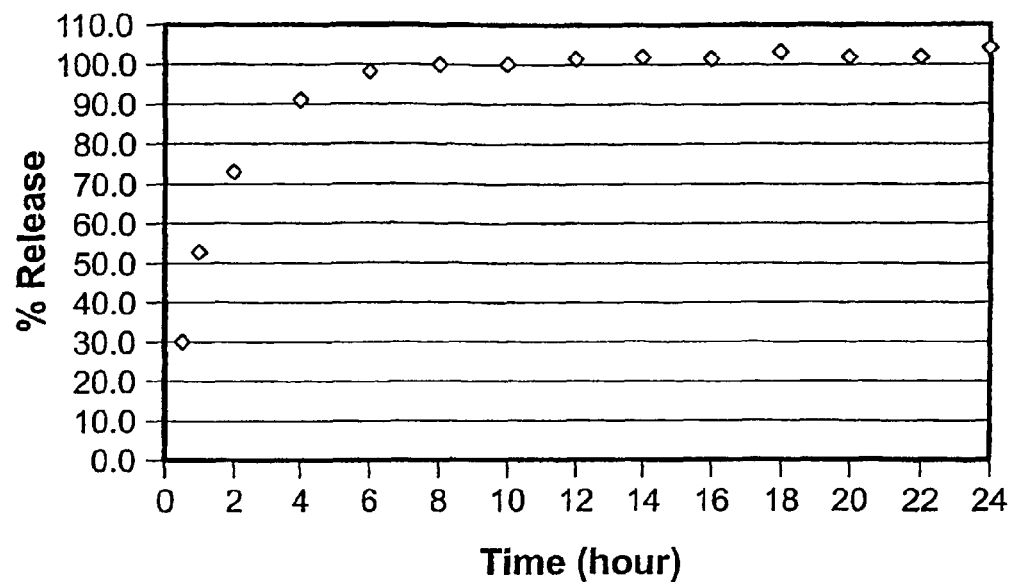
FIG. 6 is a dissolution profile of the chlorpheniramine maleate tablets of Example 6 where the pellets were made by the procedure of Example 1.
Figure 7:
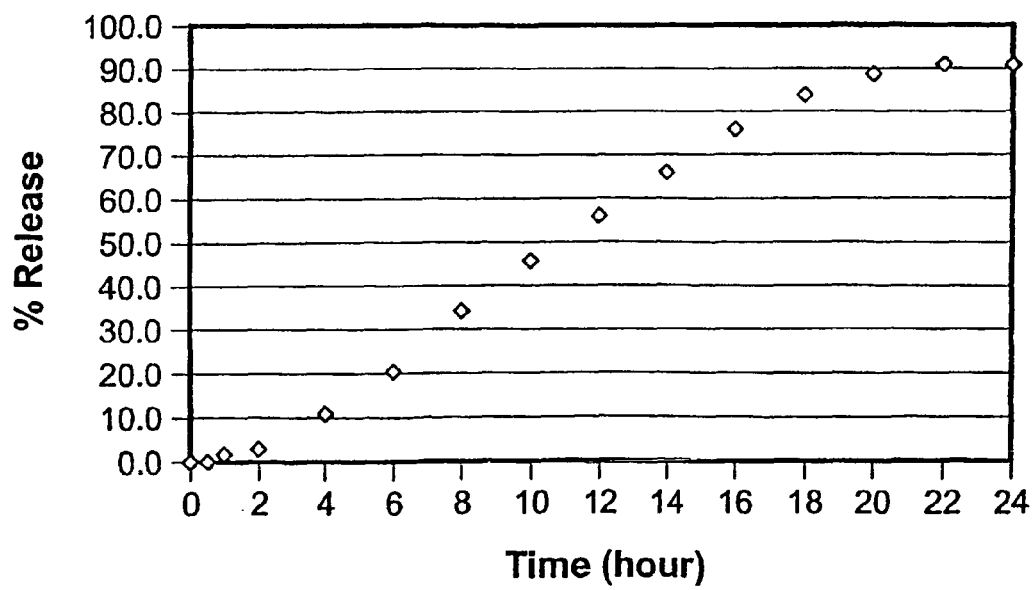
FIG. 7 is a dissolution profile of the oxybutynin chloride tablets of Example 9 where the pellets were made by the procedure of Example 1 and the combination of Carbopol 971P and 71G was used.

The term "uncoated pellet" is used to define pellets that have no coating or a coating that has no effect on the release rate of a pharmaceutical compound that is contained in the pellet. Thus in a preferred embodiment, the pellets will have no coating but it is possible to utilize pellets that have highly water soluble or highly permeable coatings that behave as if they are water soluble by not affecting the release rate of drug from a pellet. Generally, the pellets of a pharmaceutical compound will release not less than 70 wt % of pharmaceutical compound when tested in 900 ml of deionized water at 37° C., at 50-100 rpm in a USP Type 1 apparatus (basket) in two hours.

The uncoated pellets of the invention may be made using any conventional pelletizing process. It is contemplated that layering of drugs on inert cores such as sugar spheres (i.e. sucrose-starch non-pareils), microcrystalline cellulose spheres (i.e. Cellets or Cephere), solid cores such as glass beads and the like; extrusion spheronization of pellets containing a binder and/or an active drug; and the procedures of U.S. Pat. No. 6,354,728 may be used to make pellets suitable for use in the invention.

Procedures for the making of pellets by extrusion-spheronization are well known in the art. A pharmaceutically active compound and any inactive ingredients (excipients, binders etc.) are pre-mixed, then wetted with water, in a high shear mixer. The damp mass is then transferred into an extruder where it is forced through a screen or die plate, where it forms an essentially solid, cylindrical extrudate of uniform shape and size. The size of the opening in the screen or die dictate resultant pellet size. The extrudate is fed onto a rotating disk, which may be smooth or may contain a grid (waffled, grooved etc.). The extrudate breaks into small cylinders, which in time are rounded into spherically shaped solids. Subsequently, the pellets are dried to the desired residual moisture content, typically in a fluid bed dryer. Any oversized or undersized product is removed by sieving, and the resulting pellets have a narrow size distribution.

The technique of layering an active drug onto to solid core by layering is well known in the art. In solution or suspension layering, a pharmaceutically active compound and any inactive ingredients (excipients, binder etc.) are suspended or dissolved in water or an organic solvent. The resulting liquid is sprayed onto the outside of a core particle, which may be a non-pareil sugar seed (sugar sphere), microcrystalline cellulose pellets (such as Cellets or Celphere) and the like, to the desired potency. Solution or suspension layering may be conducted using a wide variety of process techniques, but a preferred method is by fluidized bed and more preferably the Wurster bottom spray method. When the desired potency has been achieved, pellets are dried to the desired residual moisture content. Any oversized or undersized product is removed by sieving, and the resulting pellets are narrow in size distribution.

Powder layering involves the application of a dry powder to some type of core material. The powder may consist entirely of a pharmaceutical compound, or may include excipients such as a binder, flow aid, inert filler, and the like. Powder layering may be conducted using a wide variety of processing techniques, but a preferred method is by rotary fluidized bed. A pharmaceutically acceptable liquid, which may be water, organic solvent, with or without a binder and/or excipients, is applied to some type of core material while applying the dry powder until the desired potency is achieved. When the desired potency has been achieved, the pellets may be seal coated to improve their strength, and are then dried to the desired moisture content. Any oversized or undersized product is removed by sieving, and the resulting pellets are narrow in size distribution.

An apparatus suitable for making pellets is disclosed in U.S. Pat. No. 6,354,728, which is incorporated by reference. This device comprises a rotor located in a chamber such that an annular gap exists between the rotor and the inner wall of said chamber. Alternatively or in addition, the rotor may contain openings in its surface allowing a gas to pass through.

The gas stream, through the openings in the rotor, may be directed such that forces acting on the pellets being formed are reduced or increased. For instance, a gas may be led through openings in the rotor from below to reduce interactions between pellets and the rotor surface as well as among the pellets. This will reduce the densification of adhering powder particles. The quantity and flow rate of the gas which is passed through the bed of the pellets should not result in a significant fluidization of the pellet bed.

The degree of densification of a pharmaceutical compound in powder form will also be influenced by the composition of the pellets being formed. One aspect of the composition of the pellets being formed is their liquid content. A higher liquid content will generally lead to a higher plasticity allowing a more effective densification. However, it has to be noted that, by the process of the invention, the degree of densification can be varied for a given composition by regulating the energy uptake of the pellets being formed when these pellets are subjected to a rolling movement, as described above.

The degree of densification of a pharmaceutical compound in powder form and any excipients/binder in the pellets made for use in the invention may be determined by the absolute porosity of the formed pellet or layer. A high porosity corresponds to a low degree of densification, and vice versa.

The porosity may be visualized by microscopic techniques, for instance by scanning electron microscopy. Alternatively, the porosity may be determined by mercury intrusion.

The degree of densification will also be reflected in the density of the pellets prepared. A higher degree of densification leads to a higher density. The achieved absolute porosity, i.e. the percentage of the total void space with respect to the bulk volume, may vary between 0.5 and 30%. Preferably, the absolute porosity has a value of from 1 to 20%, more preferably of from 1 to 10%, and especially from 2 to 10%.

The pellets of a pharmaceutical compound may be made in such a manner that the degree of densification is such that a gradient of the degree of densification in a radial direction is achieved or separate concentric zones having varying levels of densification may be formed on each pellet, either in the core or in one or more layers. The degree of densification may be controlled so that at least one layer has a density that is lower than the bulk density of the starting powder.

Generally pellets of a pharmaceutical compound according to the invention will have a diameter of from 0.01 to 2 mm, such as from 0.1 to 1.25 mm. The layer or layers will each have a layer thickness of from 0.005 to 1.0 mm, such as from 0.05 to 0.75 mm. The pellets prepared according to the invention have a narrow particle size distribution such that a maximum of 20% by weight of the pellets have a diameter deviating from the average diameter of all by more than 20%. Preferably, a maximum of 10% by weight of the pellets have a diameter deviating from the average diameter of all, by more than 20%. Further preferably, a maximum of 20% by weight of the pellets have a diameter deviating from the average diameter of all pellets by more than 10% by weight. An especially preferred pellet product has a particle size distribution such that a maximum of 10% by weight of the pellets have a diameter deviating from the average diameter of all pellets by more than 10% by weight. All percents by weight are based on the total weight of the pellets.

A preferred method of preparing pellets of a pharmaceutical compound comprises:

(a) forming a powder mixture which comprises a binder such as microcrystalline cellulose and a pharmaceutical compound;

(b) feeding said powder mixture which is optionally pre-wetted with from 0-60 wt % of a pharmaceutically acceptable liquid diluent, based on the total weight of the powder mixture and the pharmaceutically acceptable diluent, to an operating apparatus which comprises a rotor chamber having an axially extending cylindrical wall, means for passing air through said chamber from the bottom, spray means for feeding a liquid into said chamber, a rotor which rotates on a vertical rotor axis, said rotor being mounted in said rotor chamber, said rotor having a central horizontal surface and, in at least the radial outer third of said rotor, the shape of a conical shell with an outward and upward inclination of between 10° and 80°, said conical shell having a circularly shaped upper edge which lies in a plane which is perpendicular to the rotor axis, feed ports for introducing said powdered excipient, a plurality of guide vanes having an outer end affixed statically to said cylindrical wall of said rotor chamber above a plane formed by the upper edge of said conical shell of said rotor and an inner end which extends into said rotor chamber and is affixed tangentially to said cylindrical wall of said rotor chamber and having, in cross-section to the rotor axis, essentially the shape of an arc of a circle or a spiral, such that said powdered product which is circulated by kinetic energy by said rotor under the influence of kinetic energy, moves from said rotor to an inside surface of said guide vanes before falling back onto said rotor;

(c) rotating said rotor, while feeding air and spraying a pharmaceutically acceptable liquid into said rotor chamber for a sufficient amount of time to form solid pellets having a desired diameter; and (d) feeding a sufficient amount of a substantially dry, free flowing inert powder which forms a non-tacky surface when placed in contact with water to provide on said pellets an outer zone comprising a layer formed from said substantially dry, free flowing inert powder.

The pellets of a pharmaceutical compound when made in the apparatus of U.S. Pat. No. 6,354,728, which describes the use of a rotating device that propels the powder particles onto a tangentially arranged surface which causes the powder particles to roll on said tangentially arranged surface. This process results in pellets having a controlled density, for instance highly dense pellets. The pellets may be: adapted to contain high levels of a pharmaceutical compound, i.e. 1-95 wt %, and preferably from 5-90 wt % based on the total weight of the pellet with the balance being a suitable pharmaceutical excipient and/or binder. The pellets may be manufactured with a narrow size distribution without the need to carry out any substantial separation step.

The pellets for use in the invention may be prepared using an apparatus which propels particles against a tangentially arranged inner wall in such a manner that a rolling motion is imparted to the moving pellets. A liquid is fed into an apparatus such as the apparatus disclosed in U.S. Pat. No. 6,449,869 which is adapted to allow for the introduction of a powdered pharmaceutical compound during the operation of the apparatus. In one embodiment of the invention, the process of the invention involves the introduction of a pharmaceutical compound containing powder as a final step in the process in order to control and/or terminate pellet growth as well as assisting in the drying, rounding and smoothing of the pellets. The preferred apparatus is described in U.S. Pat. No. 6,449,869 and U.S. Pat. No. 6,354,728, both of which are incorporated by reference.

When core layered pellets are used, such as sugar spheres, from 20% to 99 wt %, preferably 30-80 wt % of pharmaceutical compound, may be layered onto the sugar sphere based on the total weight of the sugar sphere and the pharmaceutical compound. If desired a pharmaceutical excipient and/or binder may be used in the layering process in an amount which will be from 1-20 wt %, preferably 1-10 wt % of the total weight of the pharmaceutical compound and the excipient.

The active pharmaceutical compounds that can be delivered include inorganic and organic compounds without limitation, including drugs that act on the peripheral nerves, adrenergic receptors, cholinergic receptors, nervous system, skeletal muscles, cardiovascular system, smooth muscles, blood circulatory system, synaptic sites, neuroeffector junctional sites, endocrine system, hormone systems, immunological system, reproductive system, skeletal system, autacoid systems, alimentary and excretory systems, inhibitory of autocoid systems, alimentary and excretory systems, inhibitory of autocoids and histamine systems. The active drug that can be delivered for acting on these recipients include anticonvulsants, analgesics, anti-inflammatories, calcium antagonists, anesthetics, antimicrobials, antimalarials, antiparasitic, antihypertensives, antihistamines, antipyretics, alpha-adrenergic agonist, alpha-blockers, biocides, bactericides, bronchial dilators, beta-adrenergic blocking drugs, contraceptives, cardiovascular drugs, calcium channel inhibitors, depressants, diagnostics, diuretics, electrolytes, hypnotics, hormonals, hyperglycemics, muscle contractants, muscle relaxants, ophthalmics, psychic energizers, parasympathomimetics, sedatives, sympathomimetics, tranquilizers, urinary tract drugs, vaginal drugs, vitamins, non-steroidal anti-inflammatory drugs, angiotensin converting enzymes, polypeptide drugs, and the like.

Exemplary drugs that are very soluble in water and can be delivered by the pellets of this invention include prochlorperazine, ferrous sulfate, aminocaproic acid, potassium chloride; mecamylamine hydrochloride, procainamide hydrochloride, amphetamine sulfate, amphetamine hydrochloride, isoproteronol sulfate, methamphetamine hydrochloride, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, cimetidine hydrochloride, theophylline cholinate, cephalexin hydrochloride, oxybutynin chloride and the like.

Exemplary drugs that are poorly soluble in water and that can be delivered by the particles of this invention include diphenidol, meclizine hydrochloride, omeprazole, esomeprazole, lansoprazole, pantoprazol, prochlorperazine maleate, phenoxybenzamine, thiethylperzine maleate, anisindone, diphenadione, erythrityl tetranitrate, digoxin, isoflurophate, acetazolamide, methazolamide, bendro-flumethiazide, chlorpropamide, tolazamide, chlormadinone acetate, phenaglycodol, allopurinol, aluminum aspirin, methotrexate, acetyl sulfisoxazole, erythromycin, progestins, progestational, corticosteroids, hydrocortisone hydrocorticosterone acetate, cortisone acetate, triamcinolone, methyltestosterone, 17 beta-estradiol, ethinyl estradiol, ethinyl estradiol 3-methyl ether, prednisolone, 17 betahydroxyprogesterone acetate, non-progesterone, norgesterel, norethindrone, norethisterone, norethiederone, progesterone, norgesterone, norethynodrel, and the like.

Examples of other drugs that can be formulated according to the present invention include aspirin, indomethacin, naproxen, fenoprofen, sulindac, indoprofen, nitroglycerin, isosorbide dinitrate, timolol, atenolol, alprenolol, cimetidine, clonidine, imipramine, levodopa, chloropromazine, methyldopa, dihydroxyphenylalamine, pivaloyloxyethyl ester of alpha-methyldopa hydrochloride, theophylline, calcium gluconate, ketoprofen, ibuprofen, cephalexin, erythromycin, haloperidol, zomepirac, ferrous lactate, vincamine, diazepam, phenoxybenzamine, diltiazem, milrinone, captopril, madol, propranolol hydrochloride, quanbenz, hydrochlorothiazide, ranitidine, flurbiprofen, fenbufen, fluprofen, tolmetin, alolofenac, mefanamic, flufenamic, difuninal, nimodipine, nitrendipine, nisoldipine, nicardipine, felodipine, lidoflazine, tiapamil, gallopamil, amlodipine, mioflazine, lisinolpril, captopril, ramipril, endlapriate, famotidine, nizatidine, sucralfate, etintidine, tertatolol, minoxidil, chlordiazepoxide, chlordiazepoxide hydrochloride, diazepam, amitriptylin hydrochloride, impramine hydrochloride, imipramine pamoate, enitabas, buprorion and the like.

Other examples of pharmaceutical compounds include water soluble vitamins such as the B Vitamins, Vitamin C and the oil soluble vitamins such as Vitamin A, D, E and K. Neutraceuticals such as chondroitin, glucosamine, St. John's wort, saw palmetto and the like may also be formed into pellets according to the present invention The pharmaceutically acceptable liquid which is used in the formation of the pellets may comprise one or more components selected from the group consisting of a pharmaceutical compound, binders, diluents, disintegrants, lubricants, flavoring agents, coloring agents, surfactants, antisticking agents, osmotic agents, matrix forming polymers, film forming polymers, release controlling agents, stabilizers and mixtures thereof, in dissolved, suspended or dispersed form. Generally, only selected components will be employed to achieve the desired result for a given formulation. The particular formulation will determine if, when and how the listed components are added.

Suitable binders include materials that impart cohesive properties to a pharmaceutical compound when admixed dry or in the presence of a suitable solvent or liquid diluent. These materials commonly include starches such as pregelatinized starch, gelatin, and sugars such as sucrose, glucose, dextrose, molasses and lactose. Natural and synthetic gums include acacia, sodium alginate, extract of Irish moss, panwar gum, ghatti gum, mucilage of isapol husks, carboxymethyl cellulose, methylcellulose, microcrystalline cellulose, polyvinylpyrrolidone e.g. povidone U.S.P K30, Veegum, and larch arabogalactan. Binders are used in an effective amount, e.g. 1 to 10 wt %, based on the total weight of liquid and binder to cause a sufficient degree of agglomeration of the a pharmaceutical compound in order to allow the rapidly formation of stable particles.

Examples of pharmaceutical excipients or diluents for use in making the pellets of a pharmaceutical compound include water soluble and water insoluble materials. Examples of useful materials include microcrystalline cellulose, dicalcium phosphate, calcium sulfate, talc, an alkali metal stearate, silicon dioxide and calcium carbonate.

As noted above pellets, suitable for use in the invention, may be made by using an apparatus that is described in U.S. Pat. No. 6,354,728. That apparatus comprises a rotor chamber having an axially extending cylindrical wall, means for passing air through said chamber from the bottom, spray means for feeding a liquid into said chamber, a rotor which rotates on a vertical rotor axis, said rotor being mounted in said rotor chamber, said rotor having a central horizontal surface and, in at least the radial outer third of said rotor, the shape of a conical shell with an outward and upward inclination of between 10° and 80°, said conical shell having a circularly shaped upper edge which lies in a plane which is perpendicular to the rotor axis, feed ports for introducing said powdered excipient, a plurality of guide vanes having an outer end affixed statically to said cylindrical wall of said rotor chamber above a plane formed by the upper edge of said conical shell of said rotor and an inner end which extends into said rotor chamber and is affixed tangentially to said cylindrical wall of said rotor chamber and having, in cross-section to the rotor axis, essentially the shape of an arc of a circle or a spiral, such that said powdered product which is circulated by kinetic energy by said rotor under the influence of kinetic energy, moves from said rotor to an inside surface of said guide vanes before it falls back onto said rotor.

When the desired pellet size is substantially achieved, it is preferred to feed dry powder to the apparatus and the apparatus is allowed to run for a period of 3 to 15 minutes, and preferably 5 to 10 minutes to complete the formation of the pellets.

It is also contemplated that some additional drying at a temperature of from about 30 to 100° C., and preferably from about 40 to 90° C. until the moisture content is from 1 to 10 wt %, based on the total weight of the pellets.

The matrix forming material may be any swellable matrix forming material that provides in vitro dissolution rates of a biologically active agent within the narrow ranges required to provide the desired plasma level of the pharmaceutical compound over a desired interval which is typically 8 to 24 hours. Most matrix forming materials will also provide for the release of the pharmaceutical compound in a pH independent manner. Preferably the matrix is based on a pharmaceutically acceptable, water swellable polymer which forms a controlled release matrix. Suitable water-swellable materials for inclusion in a controlled release matrix are hydrophilic polymers, such as carbomers having a viscosity of 3,000 to 60,000 mPa s as a 0.5%-1% w/v aqueous solution, cellulose ethers such as hydroxypropylcellulose having a viscosity of about 1000-7000 mPa s as a 1% w/w aqueous solution (25° C.), hydroxypropyl methylcellulose having a viscosity of about 1000 or higher, preferably 2,500 or higher to a maximum of 25,000 mPa s as a 2% w/v aqueous solution; polyvinylpyrrolidone having a viscosity of about 300-700 mPa s as a 10% w/v aqueous solution at 20° C. Specifications for these materials are found in the Handbook of Pharmaceutical Excipients, 4th Ed, Rowe et al., Pharmaceutical Press (2003) which is incorporated by reference. Of these polymers, the carbomer polymers are preferred. In particular carbomer polymers are commercially available as Carbopol in powder (Carbopol 971P) or granular form (Carbopol 71G). A blend of carbomer in powder form (e.g. about 0.2 µm average diameter) and carbomer in granular form (e.g. about 180-425 µm average diameter) provides a desirable formulation when blended in a 10-90 wt % to 90-10 wt % ratio (granular/powder) or more preferably in a 30-70 wt % to 70-30 wt % ratio (granular/powder) based on the total weight of the carbomers.

Tablet lubricants include such well known materials as magnesium stearate, stearic acid, calcium stearate, sodium stearyl fumarate, glyceryl palmitostearate, glyceryl behenate, glyceryl monostearate, poloxamer, polyethylene glycol having a weight average molecular weight of 1000-6000 and the like.

The uncoated pellets of a pharmaceutical compound are formulated into tablets with the matrix forming polymer using conventional tabletting techniques to provide therapeutic doses which are well known to those who are skilled in the art.

The tablets of the invention may comprise:

|  | general | preferred |
|---|---|---|
| pharm. compound pellets | 10-70 wt % | 20-50 wt % |
| swellable polymer | 5-50 wt % | 5-40 wt % |
| pharmaceutical excipient | 25-85 wt % | 30-70 wt % |
| tablet lubricant | 1-10 wt % | 2-5 wt % |
| film coating | 1-10 wt % | 2-5 wt % |

(based on the total weight of the tablet)

DESCRIPTION OF THE PREFERRED EMBODIMENTS

Example 1

A granular form of carbomer (Carbopol 71G) is used to prepare oxybutynin chloride pellets as follows:

| Procedure: Blend | |
|---|---|
| Oxybutynin HCl | 15.0% |
| Microcrystalline cellulose | 56.7% |
| Dicalcium Phosphate | 28.3% |

Load the above ingredients (total weight of blend 16 Kg) in a vertical high shear granulator for 2 min.
Weigh 3.2 Kg of the blend for powder feeding portion
Spray 4.5 Kg of water at 500 g/min spray rate, atomization air pressure 2.0 bar.

Discharge the blend from high shear granulator, load the blend into an apparatus as described in U.S. Pat. No. 6,354,728.

Start the apparatus and spray water at 250 g/min.
Process conditions follow:
  Inlet air temperature 17° C.
  Rotor speed 500 rpm initial, reduced to 250 rpm after 1.6 Kg of water applied.
  After 7.1 Kg of water applied, start powder feed at 235 g/min.
  Stop process after 8.6 Kg water is applied.
Discharge the wet pellets. Dry in a fluid bed dryer.
Final moisture 1.71%

The pellets were sieved to obtain a fraction of 25/35 US Standard mesh or 500-710 microns.

| Tablet formulation: | Quantity |
|---|---|
| Oxybutynin Pellets (15%) | 455.0 g |
| Microcrystalline cellulose | 385.0 g |
| Carbopol 71G | 120.0 g |
| Stearic acid | 40.0 g |
| Total | 1000.0 g |

The tablet ingredients are mixed in a 8 qt. V blender and compressed in a 6 station tablet press (Korsch, model PH106) to make standard concave round 9/32" tablets.

The dissolution profiles of these tablets, (uncoated oxybutynin chloride pellets made with a granular carbomer matrix) was determined in a USP Type 2 apparatus, using pH 6.8 phosphate buffer at 37° C. and 50 rpm.

| Time (hour) | % Release |
|---|---|
| 0.0 | 0.0 |
| 0.5 | 0.5 |
| 1.0 | 1.8 |
| 2.0 | 5.2 |
| 4.0 | 16.6 |
| 6.0 | 28.7 |
| 8.0 | 40.6 |
| 10.0 | 52.1 |
| 12.0 | 63.2 |
| 14.0 | 73.8 |
| 16.0 | 83.5 |
| 18.0 | 87.1 |
| 20.0 | 88.4 |
| 22.0 | 88.7 |
| 24.0 | 88.4 |

Example 2

Propranolol Extended Release Tablets

| Propranolol Pellets composition | |
|---|---|
| Propranolol HCl | 60% |
| Microcrystalline cellulose | 40% |

Propranolol pellets were prepared using the procedure of Example 1. Pellet size used for subsequent tableting is 30/80 mesh (180-600 micron)

| Tablet Formulation: | Quantity |
|---|---|
| Propranolol HCl Pellets | 225.0 g |
| Microcrystalline cellulose | 215.0 g |
| Carbopol 971P | 40.0 g |
| Stearic Acid | 20.0 g |
| Total | 500.0 g |

Tablets were made using a rotary tablet press Korsch PH106, with round standard concave, 11/32 inch diameter, tablet tooling. Target tablet weight is 296.2 mg. Propranolol HCl content is 80 mg per tablet.

The dissolution Profile of Propranolol Extended Release Tablets (Uncoated propranolol pellets made with a powdered carbomer matrix as in Example 1) obtained as described in Example 1.

| Time (hr) | % Release |
|---|---|
| 0.0 | 0.00 |
| 0.5 | 6.20 |
| 1.0 | 12.80 |
| 2.0 | 21.20 |
| 3.0 | 27.10 |
| 4.0 | 31.80 |
| 5.0 | 36.30 |
| 6.0 | 40.60 |
| 8.0 | 48.70 |
| 10.0 | 56.60 |
| 12.0 | 64.30 |
| 14.0 | 71.50 |
| 16.0 | 79.50 |
| 18.0 | 88.20 |
| 18.5 | 91.10 |

The zero order release profile was achieved for propranolol HCl, which has different chemical and solubility characteristics than oxybutynin chloride was similar to the zero order release profile achieved with oxybutynin chloride. The uncoated propranolol HCl pellets contained 60% of propranolol HCL as compared to 15% oxybytynin chloride pellets in Example 1. The tablet dimensions for propranolol HCl extended release tablets was also different from that of oxybutynin chloride extended release tablets.

Example 3

Propranolol Extended Release Tablets

| Propranolol Pellets composition | |
|---|---|
| Propranolol HCl | 60% |
| Microcrystalline cellulose | 40% |

Propranolol pellets were prepared using extrusion/spheronization, single screw extruder model E 35 T, WLS Gabler. Blend of Propranolol HCl and microcrystalline cellulose 1000 g was moisted with water and extruded using cartridge size 0.8/1.0 mm at speed setting 5. After the speronization and drying step in the rotor, the pellets were sieved to 250-560 μm fraction.

| Tablet Formulation: | Quantity |
|---|---|
| Propranolol HCl Pellets | 15.0 g |
| Microcrystalline cellulose | 14.3 g |

| Tablet Formulation: | Quantity |
|---|---|
| Carbopol 971P | 2.7 g |
| Stearic Acid | 1.3 g |
| Total | 33.3.0 g |

Tablet using rotary tablet press Korsch PH106, tablet tooling is round standard concave, 11/32 inch diameter. Target tablet weight is 296.2 mg. Propranolol HCl content is 80 mg per tablet.

Dissolution Profile of Propranolol HCl Extended Release Tablets (Uncoated Propranolol HCl Pellets Made with a Powder Carbomer Matrix).

| Time (hr) | % Release |
|---|---|
| 0.5 | 5.2 |
| 1.0 | 10.9 |
| 2.0 | 18.6 |
| 4.0 | 27.7 |
| 6.0 | 34.3 |
| 8.0 | 41.2 |
| 10.0 | 47.8 |
| 12.0 | 56.0 |
| 14.0 | 64.8 |
| 16.0 | 74.8 |
| 18.0 | 83.6 |
| 20.0 | 88.7 |
| 22.0 | 89.8 |
| 24.0 | 92.3 |

Similar zero-order release profile was also achieved for Propranolol, where propranolol pellets were produced using extrusion/spheronization process. The uncoated Propranolol pellets in this example (Example 3 were produced using different process than direct pelletization, used to produce Propranolol pellets in Example 2.

Example 4

Metoprolol Succinate Extended Release Tablets

Metoprolol Succinate Pellets were produced using sugar spheres as starting core pellets. These were layered with a 30% w/w solution of metopropol succinate in water with a small quantity of silicon dioxide (3.75% of the weight of the metoprolol succinate) added as an anti-tacking agent. Pellet size was used for subsequent tabletting is 25/40 mesh (425-710 microns).

| Metoprolol Pellet Composition | |
|---|---|
| Sugar Spheres 50/70 mesh | 1.6 Kg |
| Metoprolol Succinate | 6.4 Kg |
| Silicon dioxide | 0.24 Kg |

Uncoated metoprolol succinate pellets were immediate release, with not less than 75% released in 30 minutes when tested in water in a USP Type 1 apparatus at 37° C. at 50 rpm.

| Tablet Formulation: | Quantity |
|---|---|
| Metoprolol Succinate Pellets | 77.7 g |
| Microcrystalline cellulose | 144.8 g |
| Carbopol 971P | 20.0 g |
| Stearic Acid | 7.5 g |
| Total | 250.0 g |

Tablet using rotary tablet press Korsch PH106, tablet tooling is round standard concave, 7/16 inch diameter. Target tablet weight is 730.1 mg. Metoprolol succinate content is 176 mg per tablet.

The dissolution Profile of Metoprolol Succinate Extended Release Tablets (uncoated metoprolol succinate pellets made with a powder carbomer magtrix) was obtained as described in Example 1.

| Time (hour) | % Release |
|---|---|
| 0 | 0.00 |
| 1 | 10.20 |
| 2 | 18.60 |
| 4 | 31.50 |
| 6 | 42.50 |
| 8 | 53.20 |
| 10 | 66.40 |
| 12 | 79.30 |
| 14 | 88.60 |
| 16 | 95.20 |
| 18 | 99.40 |
| 20 | 101.10 |

Similar zero-order release profile was also achieved for metoprolol succinate, which has different chemical and solubility characteristics than oxybytynin chloride. Metoprolol succinate pellets contained 77.7% of metoprolol succinate as compared to 15% oxybytynin pellets in Example 1. Moreover, the metoprolol succinate pellets were produced using drug layering process onto sugar spheres which was different process than direct pelletization, used to produce oxybutynin chloride pellets. The tablet dimensions for the metoprolol succinate extended release tablets was also different than that of oxybutynin chloride extended release tablets.

Example 5

Ibuprofen Extended Release Tablets

| Ibuprofen Pellet Composition: | |
|---|---|
| Ibuprofen | 90% |
| Microcrystalline cellulose | 10% |

The pellets were made by the same technique that is described in Example 1.

| Ibuprofen Pellets Particle Size Distribution | |
|---|---|
| Sieve # | % Retained |
| 20 | 3.7 |
| 40 | 19.6 |
| 60 | 38.4 |
| 80 | 10.8 |

-continued

| Ibuprofen Pellets Particle Size Distribution | |
|---|---|
| Sieve # | % Retained |
| 100 | 9.8 |
| 200 | 10 |
| Pan | 7.6 |

Note:
Particle size distribution of Ibuprofen pellets is not as narrow as pellets in other examples.

| Tablet Formulation: | Quantity |
|---|---|
| Ibuprofen Pellets | 226.0 g |
| Microcrystalline cellulose | 214.0 g |
| Carbopol 971P | 40.0 g |
| Stearic acid | 20.0 g |
| Total | 500.0 g |

Tablet using rotary tablet press Korsch PH106, tablet tooling is round standard concave, $11/32$ inch diameter. Target tablet weight is 296.2 mg. Ibuprofen content is 120 mg per tablet.

Dissolution Profile of Ibuprofen Extended Release Tablets (Uncoated Ibuprofen Pellets in Carbopol Matrix) in Phosphate Buffer at pH 7.2, 50 Rpm in a USP Type 2 Apparatus at 37° C.:

| Time (hours) | % Release |
|---|---|
| 0.5 | 0.9 |
| 1.0 | 1.9 |
| 2.0 | 5.2 |
| 4.0 | 17.6 |
| 6.0 | 37.6 |
| 8.0 | 60.4 |
| 10.0 | 78.5 |
| 12.0 | 93.7 |
| 14.0 | 102.3 |
| 16.0 | 110.3 |
| 18.0 | 115.5 |
| 20.0 | 118.0 |
| 22.0 | 119.8 |
| 24.0 | 120.9 |

A zero-order release profile, similar to the profile of the oxybutynin chloride of Example 1 was also achieved for Ibuprofen, which has different chemical and solubility characteristics than oxybytynin chloride. Ibuprofen pellets contained 90% of ibuprofen as compared to the 15% oxybytynin chloride pellets of Example 1. Particle size distribution of Ibuprofen pellets was wide range (approx. 75 to 425 micron). Tablet dimension for Ibuprofen extended release tablets was also different than that of Oxybutynin extended release tablets.

Example 6

Chlorpheniramine Maleate Extended Release Tablets

| Chlorpheniramine Maleate Pellet Composition: | |
|---|---|
| Chlorpheniramine Maleate | 10% |
| Microcrystalline cellulose | 90% |

Chlorpheniramine Maleate pellets were prepared using the procedure of Example 1. The pellet size range used for subsequent tableting is 40/80 mesh (180-447 micron).

Dissolution of Chlorpheniramine Maleate Pellets in a USP Apparatus Type 1, in Water at 100 Rpm at 37° C.:

| Time | % Dissolved |
|---|---|
| 15 min | 93.0 |
| 60 min | 92.6 |
| Infinity | 92.1 |

| Tablet Formulation: | Quantity |
|---|---|
| Chlorpheniramine Maleate Pellets | 225.0 g |
| Microcrystalline cellulose | 215.0 g |
| Carbopol 971P | 40.0 g |
| Stearic acid | 20.0 g |
| Total | 500.0 g |

Dissolution Profile of Chlorpheniramine Maleate Extended Release Tablets (Uncoated Chlorpheniramine Maleate Pellets in Powdered Carbomer Matrix) in 0.01N HCl Using a USP Type 2 Apparatus at 37° C. at 50 Rpm:

| Time (hr) | % Release |
|---|---|
| 0.5 | 30.2 |
| 1 | 53.2 |
| 2 | 73.4 |
| 4 | 91.2 |
| 6 | 97.9 |
| 8 | 99.6 |
| 10 | 100.2 |
| 12 | 101.5 |
| 14 | 102.3 |
| 16 | 101.6 |
| 18 | 103.0 |
| 20 | 102.1 |
| 22 | 102.2 |
| 24 | 103.5 |

Sustained release was observed for Chlorpheniramine maleate extended release tablets, when compared to uncoated chlorpheniramine maleate pellets (93% release in 15 min) in water in a USP Type 1 apparatus in water at 37° C. and 100 rpm.

In Examples 1 to 5, various uncoated drug pellets at various concentration of drug in the pellet (10 to 90%) were formulated into matrix tablets with a carbomer, at 8% concentration of the carbomer in the finished tablet. Drug concentration in tablets in Example 1 to 6 varies based on therapeutic dose of each drug. Zero order drug release profiles in 24 hours were obtained in Example 1 to 5. In Example 6, extended first order drug release was obtained.

Uncoated Oxybutynin Pellets in Matrix Tablets

Oxybytynin Chloride pellets were produced using the procedure of Example 1. The formulation of oxybutynin chloride pellets in each example (Examples 7-9) contained 15% of oxybutynin chloride but varied slightly in excipients and quantity of excipients. Several hydrophilic matrix polymers have been investigated to produce extended release oxybutynin chloride tablets.

Changing the composition of the oxybutynin chloride pellet and changing the controlled release polymer in the matrix tablet formulations affected the dissolution profile of the oxybutynin chloride extended release tablets.

Example 7

Oxybutynin Chloride Pellets were prepared according to the procedure of Example 1.

| | |
|---|---|
| Oxybutynin HCl | 15.0% |
| Microcrystalline cellulose | 56.7% |
| Dicalcium Phosphate | 28.3% |

Dissolution of Oxybytynin Chloride Pellets in pH 6.8 Phosphate Buffer

| Time (min) | % Release |
|---|---|
| 15 | 48.5 |
| 30 | 55.5 |
| 45 | 60.5 |
| 60 | 64.0 |
| 120 | 74.5 |

| Tablet formulation: | Quantity |
|---|---|
| Oxybutynin chloride pellets | 238.6 g |
| Microcrystalline cellulose | 178.4 g |
| Carbopol 971P | 79.5 g |
| Magnesium Stearate | 3.5 g |
| Total | 500.0 g |

Tablet tooling is standard concave, round 9/32 inch

Dissolution Profile of Oxybutynin Chloride Extended Release Tablets (Oxybutynin pellets in Carbopol matrix) according to the procedure of Example 1:

| Time (hour) | % Release |
|---|---|
| 0 | 0.0 |
| 0.5 | 0.7 |
| 1 | 1.1 |
| 2 | 2.6 |
| 3 | 4.5 |
| 4 | 6.3 |
| 5 | 8.9 |
| 6 | 11.5 |
| 7 | 13.9 |
| 8 | 16.3 |
| 9 | 20.5 |
| 10 | 24.6 |
| 11 | 28.0 |
| 12 | 31.3 |
| Infinity | 74.8 |

Zero order release for 24 hours of oxybutynin chloride was observed. The uncoated oxybutynin chloride pellets in a carbomer matrix released oxybutynin chloride slowly and consistently.

Example 8

Oxybutynin Chloride Pellets were prepared as described in Example 1:

| | |
|---|---|
| Oxybutynin HCl | 15.0% |
| Microcrystalline cellulose | 28.3% |
| Dicalcium Phosphate | 56.7% |

Dissolution of Oxybutynin Chloride Pellets in pH 6.8 Phosphate Buffer in a USP Type 2 Apparatus at 37° C. at 50 rpm:

| Time (min) | % Release |
|---|---|
| 15 | 81.8 |
| 30 | 85.7 |
| 45 | 88.4 |
| 60 | 90.5 |
| 120 | 94.2 |

| Tablet formulation: | Quantity |
|---|---|
| Oxybutynin Chloride Pellets | 221.2 g |
| Microcrystalline cellulose | 54.8 g |
| Methocel K4M | 120.0 g |
| Magnesium Stearate | 4.0 g |
| Total | 400.0 g |

Tablet tooling is standard concave, round 9/32 inch

Dissolution Profile of Oxybutynin Chloride Extended Release Tablets (Uncoated Oxybutynin Pellets in Methocel K4M Matrix) Using the Method of Example 1.

| Time (hour) | % Release |
|---|---|
| 0 | 0.0 |
| 0.5 | 8.5 |
| 1 | 12.9 |
| 2 | 20.0 |
| 3 | 24.3 |
| 4 | 28.5 |
| 5 | 32.2 |
| 6 | 35.8 |
| 7 | 38.1 |
| 8 | 42.3 |
| 9 | 44.9 |
| 10 | 47.5 |
| 11 | 49.5 |
| 12 | 51.4 |
| Infinity | 89.4 |

Zero-order drug release in approximately 24 hours was observed using Methocel K4M with uncoated oxybutynin chloride pellets. Friability is 8.1%. The tablet formulation may be modified by adding a minor amount of a binder (5 wt % of povidone K30), based on the total weight of the tablet.

Changes in uncoated drug pellet composition, types and concentration of the controlled release polymers can result in desirable drug dissolution profiles. Adjustment in the tablet formulation can improve the tabletting process of particular formulation.

Comparative Examples

Oxybutynin chloride powder at the same dose (15 mg per tablet) was mixed with excipient and Carbopol 971P (8% in the formulation). Using the same tablet tooling (9/32 inch round) and the same target tablet weight, dissolution results were compared.

| Tablet formulation: | Quantity |
| --- | --- |
| Control | |
| Oxybutynin Chloride | 35.8 g |
| Microcrystalline cellulose | 404.2 g |
| Carbopol 971P | 40.0 g |
| Stearic acid | 20.0 g |
| Total | 500.0 g |
| Invention | |
| Oxybutynin Pellets (15%) | 455.0 g |
| Microcrystalline cellulose | 425.0 g |
| Carbopol 971P | 80.0 g |
| Stearic acid | 40.0 g |
| Total | 1000.0 g |

+Both samples contained Carbopol 971P 8% in the formulation.
Testing conditions corresponded to Example 1:

| Time (hour) | Invention (Oxybytynin Pellets in Carbopol matrix) % Release | Control (Oxybutynin powder in Carbopol matrix) % Release |
| --- | --- | --- |
| 0.0 | 0.0 | 0.0 |
| 0.5 | 1.0 | 2.6 |
| 1.0 | 2.0 | 4.0 |
| 2.0 | 4.9 | 6.3 |
| 4.0 | 13.2 | 9.5 |
| 6.0 | 22.9 | 12.5 |
| 8.0 | 34.6 | 16.4 |
| 10.0 | 43.9 | 20.5 |
| 12.0 | 58.8 | 24.5 |
| 14.0 | 70.6 | 27.9 |
| 16.0 | 82.2 | 31.4 |
| 18.0 | 89.0 | 34.8 |
| 20.0 | 95.3 | 37.5 |
| 22.0 | 97.4 | 40.3 |
| 24.0 | 98.5 | 43.2 |

The zero-order release of oxybutynin chloride over 24 hours time period was achieved in the case of the Invention (Uncoated oxybutynin chloride pellets in Carbopol matrix). When oxybutynin chloride powder (instead of pellets) was blended with tablet excipients and Carbopol, zero-order release of oxybutynin chloride was observed but only 43% of the drug release in 24 hours.

The zero-order drug release over 24 hours is useful for once-a-day medication.

Example 9

In this Example, a blend of a granular form of carbomer (i.e. Carbopol 71G) is used in combination with a powder form of carbomer (Carbopol 971P).

| Oxybutynin Pellets | |
| --- | --- |
| Oxybutynin HCl | 15.0% |
| Microcrystalline cellulose | 70.9% |
| Dicalcium Phosphate | 14.1% |

| Tablet formulation: | Quantity |
| --- | --- |
| Oxybutynin Pellets (15%) | 227.5 g |
| Microcrystalline cellulose | 177.5 g |
| Carbopol 71G | 50.0 g |
| Carbopol 971P | 25.0 g |
| Stearic acid | 20.0 g |
| Total | 500.0 g |

Dissolution Profiles of Oxybutynin Extended Release Tablets, (Uncoated Oxybutynin Chloride Pellets in a Matrix Comprising Carbopol 971P (5%) and 71G (15%) Combination).

The release profile was determined as in Example 1.

| Time (hour) | % Release |
| --- | --- |
| 0.0 | 0.0 |
| 0.5 | 0.5 |
| 1.0 | 1.4 |
| 2.0 | 3.5 |
| 4.0 | 10.8 |
| 6.0 | 20.7 |
| 8.0 | 33.4 |
| 10.0 | 45.7 |
| 12.0 | 56.1 |
| 14.0 | 66.0 |
| 16.0 | 75.8 |
| 18.0 | 83.8 |
| 20.0 | 88.7 |
| 22.0 | 90.6 |
| 24.0 | 90.8 |

As compared to Example 1, this Example used the same uncoated oxybutynin chloride pellets in a matix formulation based on powder and granular carbomer. A similar zero order release of oxybytynin chloride in 24 hours was achieved.

The invention claimed is:

1. A compressed tablet which provides zero-order release of a pharmaceutical compound, comprising:
   a matrix which comprises:
   uncoated pellets comprising the pharmaceutical compound; and
   a water-swellable polymer which controls a release of the pharmaceutical compound;
   wherein said uncoated pellets have an absolute porosity of from 2-10%; and
   wherein the compressed tablet provides zero-order release of the pharmaceutical compound for at least the first 4 hours after administration of the compressed tablet.

2. The compressed tablet as defined in claim 1;
   wherein the uncoated pellets further comprise a pharmaceutical excipient.

3. The compressed tablet as defined in claim 2;
   wherein the pharmaceutical excipient is selected from the group consisting of microcrystalline cellulose, dicalcium phosphate, calcium sulfate, talc, silicon dioxide and calcium carbonate.

4. The compressed tablet as defined in claim 2;
   wherein the water-swellable polymer is carbomer.

5. The compressed tablet as defined in claim 1;
   wherein the uncoated pellets further comprise microcrystalline cellulose and dicalcium phosphate;
   wherein the water-swellable polymer is carbomer; and
   wherein the matrix further comprises microcrystalline cellulose polymer.

6. The compressed tablet as defined in claim 1;
where the pharmaceutical compound is ibuprofen.

7. The compressed tablet as defined in claim 1;
where the pharmaceutical compound is oxybutynin chloride.

8. The compressed tablet as defined in claim 1;
where the pharmaceutical compound is metoprolol succinate.

9. The compressed tablet as defined in claim 1;
where the pharmaceutical compound is propranolol hydrochloride.

10. The compressed tablet as defined in claim 1;
where the pharmaceutical compound is chlorpheniramine maleate.

11. A method of making the tablet defined in claim 1, the method comprising:
   (a) preparing uncoated pellets comprising the pharmaceutical compound;
   (b) dispersing said uncoated pellets in a matrix which comprises the water-swellable polymer; and
   (c) compressing said matrix into a tablet;
   wherein said uncoated pellets have an absolute porosity of from 2-10%.

12. The method as defined in claim 11;
wherein the uncoated pellets further comprise a pharmaceutical excipient.

13. The method as defined in claim 12;
wherein the pharmaceutical excipient is selected from the group consisting of microcrystalline cellulose, dicalcium phosphate, calcium sulfate, talc, silicon dioxide, and calcium carbonate.

14. The method of making a tablet as defined in claim 11;
wherein the water-swellable polymer is carbomer.

15. The method of making a tablet as defined in claim 12;
wherein the water-swellable polymer is carbomer.

16. The compressed tablet of a pharmaceutical compound as defined in claim 1;
wherein the swellable water-swellable polymer is selected from the group consisting of carbomer, hydroxy propyl cellulose, hydroxypropyl methylcellulose, and polyvinylpyrrolidone.

17. The compressed tablet of a pharmaceutical compound as defined in claim 1;
wherein said uncoated pellets are substantially spherically shaped, having an aspect ratio, derived by dividing a length of the pellet by a width of the pellet, in a range of from 1.0 to less than 1.4.

18. The method of making a tablet as defined in claim 11;
wherein the uncoated pellets further comprise microcrystalline cellulose and dicalcium phosphate;
wherein the water-swellable polymer is carbomer; and
wherein the matrix further comprises microcrystalline cellulose.

19. The compressed tablet as defined in claim 1;
wherein the compressed tablet provides release of at least 50% of the pharmaceutical compound by 24 hours after administration of the compressed tablet.

20. The compressed tablet as defined in claim 1;
wherein the water-swellable polymer is carbomer.

21. The compressed tablet as defined in claim 1;
wherein the compressed tablet provides release of at least 80% of the pharmaceutical compound by 24 hours after administration of the compressed tablet.

22. The method of making a tablet as defined in claim 11;
wherein the water-swellable polymer is selected from the group consisting of carbomer, hydroxy propyl cellulose, hydroxypropyl methylcellulose, and polyvinylpyrrolidone.

23. The method of making a tablet as defined in claim 11;
wherein said uncoated pellets are substantially spherically shaped, having an aspect ratio, derived by dividing a length of the pellet by a width of the pellet, in a range of from 1.0 to less than 1.4.

24. The compressed tablet as defined in claim 1;
wherein the uncoated pellets are subject to a rolling movement while regulating their energy uptake in order to created the absolute porosity.

\* \* \* \* \*